United States Patent [19]

Schwan

[11] 4,113,743
[45] Sep. 12, 1978

[54] 2-[[6-METHOXY-(3,4-DIHYDRO-2H-1-BENZOPYRANYL)]AMINO]-1-PHENYL-PROPANOL HYDROCHLORIDE

[75] Inventor: Thomas J. Schwan, Norwich, N.Y.

[73] Assignee: Morton-Norwich Products. Inc., Norwich, N.Y.

[21] Appl. No.: 783,811

[22] Filed: Apr. 1, 1977

[51] Int. Cl.² .................... C07D 311/02; A01K 31/35
[52] U.S. Cl. ................................. 260/345.5; 424/283
[58] Field of Search .......... 260/345.2, 345.5, 345.7 R, 260/345.8 R

[56] References Cited

U.S. PATENT DOCUMENTS 3,468,897   9/1969   Fournari et al. .................. 260/345.2
3,901,945   8/1975   Uyeda .............................. 260/566 R

OTHER PUBLICATIONS

Roberts et al., "Basic Principles of Organic Chemistry," pp. 449-453 (1965).
Sandler et al., "Organic Functional Group Preparations," vol. 12-II, pp. 246-257 (1971).
Sandler et al., "Organic Functional Group Preparations," vol. 12, pp. 336 to 337 (1968).

*Primary Examiner*—Nicky Chan
*Attorney, Agent, or Firm*—Anthony J. Franze

[57] ABSTRACT

A compound 2-[[6-methoxy-(3,4-dihydro-2H-1-benzopyranyl)]amino]-1-phenylpropanol hydrochloride possesses pharmacologic activity as an antidepressant.

1 Claim, No Drawings

2-[[6-METHOXY-(3,4-DIHYDRO-2H-1-BENZOPYRANYL)]AMINO]-1-PHENYLPROPANOL HYDROCHLORIDE

This invention relates to a chemical compound. In particular it is concerned with the compound 2-[[6-methoxy-(3,4-dihydro-2-H-benzopyranyl)]amino]-1-phenylpropanol hydrochloride.

This compound possesses pharmacologic activity affecting the central nervous system. When administered perorally to animals it exhibits antidepressant action. Its antidepressant property is evidenced in the control of tetrabenazine-induced ptosis in mice. An oral dose of 50 mg/kg of this compound to mice intraperitoneally receiving 35 mg/kg of tetrabenazine counteracts to ptosis producing property of tetrabenazine.

In order that this invention be readily available to and understood by those skilled in the art, the following illustration is included:

2-[[6-Methoxy-(3,4-dihydro-2H-1-benzopyranyl)]-amino]-1-phenylpropanol hydrochloride A mixture of 17.8 g (0.10 mole) of 2,3-dihydro-6-methoxy-4H-1-benzopyran-4-one, 15.1 g (0.10 mole) 2-amino-1-phenylpropanol, 2.0 g p-toluenesulfonic acid monohydrate and 250 ml toluene was stirred and refluxed for 16 hrs using a Dean Stark apparatus. Amount $H_2O$ evolved: 1.70 ml. Another 1.0 g of the sulfonic acid was added. An additional one hour reflux time resulted in the evolution of another 0.20 ml of $H_2O$.

The mixture was concentrated to dryness in vacuo and the residue was dissolved in 250 ml $CH_3OH$. The solution was cooled at 10°–15° while sodium borohydride (3.80 g, 0.10 mole) was added over 10 min. The reaction mixture was stirred at ambient temperature for 1.5 hr, diluted with 450 ml water, and extracted with 2 × 200 ml $CHCl_3$. The combined extracts were washed with 200 ml water, dried over $MgSO_4$, and concentrated to dryness in vacuo.

To an ethanolic solution of the residue was added ethanolic HCl. The solution was concentrated to dryness in vacuo. Recrystallization from acetonitrile gave, in two crops, 6.60 g (19%) of the product, m.p. 184°–201°. An analytical sample, m.p. 216°–217°, was obtained by recrystallization from acetonitrile.

Anal. Calcd. for $C_{19}H_{23}NO_3 \cdot HCl$: C, 65.19; H, 6.91; N, 4.00. Found: C, 65.02; H, 6.94; N, 3.92.

What is claimed is:

1. The compound 2-[[6-methoxy-(3,4-dihydro-2H-1-benzopyranyl)]amino]-1-phenylpropanol hydrochloride.